United States Patent [19]

Gerlinger et al.

[11] Patent Number: 4,756,619

[45] Date of Patent: Jul. 12, 1988

[54] REFLECTANCE MEASURING APPARATUS FOR MAKING CONTACTLESS MEASUREMENTS

[75] Inventors: Hermann Gerlinger, Aalen-Ebnat; Gerhard Hohberg, Oberkochen, both of Fed. Rep. of Germany

[73] Assignee: Carl-Zeiss-Stiftung, Heidenheim, Fed. Rep. of Germany

[21] Appl. No.: 889,330

[22] Filed: Jul. 23, 1986

[30] Foreign Application Priority Data

Jul. 25, 1985 [DE] Fed. Rep. of Germany ....... 3526553

[51] Int. Cl.⁴ .......................... G01J 3/36; G01J 3/42; G01N 21/86; G01N 21/47
[52] U.S. Cl. .................................. 356/319; 356/328; 356/446; 356/429
[58] Field of Search ............... 356/243, 308, 319, 326, 356/328, 429, 430, 435, 446, 448; 250/571

[56] References Cited

U.S. PATENT DOCUMENTS

| | | | |
|---|---|---|---|
| 3,718,399 | 2/1973 | Kalman | 356/446 X |
| 3,743,430 | 7/1973 | Riggs | 356/435 |
| 3,973,849 | 8/1976 | Jackson et al. | 356/308 |
| 4,003,660 | 1/1977 | Christie Jr. et al. | 356/448 X |
| 4,076,421 | 2/1978 | Kishner | 356/236 X |
| 4,093,385 | 6/1978 | Noboru | 356/243 X |
| 4,319,847 | 3/1982 | Howarth | 250/571 X |
| 4,449,821 | 5/1984 | Lee | 356/319 |
| 4,568,191 | 2/1986 | Barry | 356/446 |

*Primary Examiner*—Vincent P. McGraw
*Attorney, Agent, or Firm*—Walter Ottesen

[57] ABSTRACT

A reflectance measuring apparatus for contactless measurement is described, in which the result of measurement is not dependent on the distance from the test object within a predetermined range. This is attained by disposing the light source in the focus of a condenser, and by providing that the measuring area is smaller than the core region inside the irradiated area on the surface of the test object.

10 Claims, 2 Drawing Sheets

REFLECTANCE MEASURING APPARATUS FOR MAKING CONTACTLESS MEASUREMENTS

FIELD OF THE INVENTION

The invention relates to a reflectance measuring apparatus for contactless measuring, for instance, on a moving band or other moving surface. The apparatus includes a stationary light source for illuminating an irradiated area on the surface of the test object and has a measuring device for detecting the radiation reflected by a measuring area on the surface of the test object with the irradiated area being larger than the measuring area.

BACKGROUND OF THE INVENTION

An apparatus of the kind referred to above is disclosed in German patent No. 16 22 484. In this apparatus, a small region of a moving band is illuminated by a pulsed light source and an image of a diaphragm illuminated by the light source is formed on the band. German patent No. 16 22 484 refers to this irradiated area as being a field limiting image. An image of a middle zone of this irradiated area is formed on a receiver, so that the measuring area from which the reflected radiation is detected by the measuring device is smaller than the irradiated area. This known apparatus has the disadvantage that the measurement result is dependent on the distance between the band and the measuring device. In many machines in which the reflectance or the color of moving bands must be measured, however, this distance is not constant, because at the locations where it is possible to accommodate a measuring device, the band flutters.

SUMMARY OF THE INVENTION

Accordingly, it is an object of the invention to provide a reflectance measuring apparatus in which the result of measurement is practically unaffected by the distance between the test object and the measuring apparatus within a predetermined range.

This object is realized in the apparatus according to the invention in that the intensity of the illumination of the surface of the test object inside the measuring area is virtually independent of the distance between the surface of the test object and the illuminating and measuring apparatus.

Pursuant to an advantageous embodiment of the invention, the light source is mounted in the focus of a condenser and the measuring area is smaller than the core area of the irradiated area when the surface of the test object is at the maximum possible distance from the illuminating and measuring apparatus.

With a point source of light and a condenser that is free of image distortion, the collimated beam would effect the same intensity of illumination at every distance. The finite size of the light source results in a divergence which causes a distance-dependent deterioration at the edge. Within a certain core region, however, the intensity of the illumination remains independent of the distance. The prerequisite for measurement not dependent upon distance is therefore that the measuring apparatus detect only returned radiation from this core region, that is, that the measuring area be smaller than the core region. Another prerequisite is that the aperture of the measuring device be constant and this prerequisite is fulfilled in German patent No. 16 22 484. In other words, the spatial angle detected by the receiver or the measuring device must be constant.

A particular advantage of the invention is that because measurement is not dependent on distance, the measurement results can be used not only for documentation but also for direct process control, for instance for varying the mixture in paper making, or the roller pressure in textile dyeing.

BRIEF DESCRIPTION OF THE DRAWING

The invention will now be described with reference to the drawing wherein.

DESCRIPTION OF THE PREFERRED EMBODIMENTS OF THE INVENTION

Figure 1:
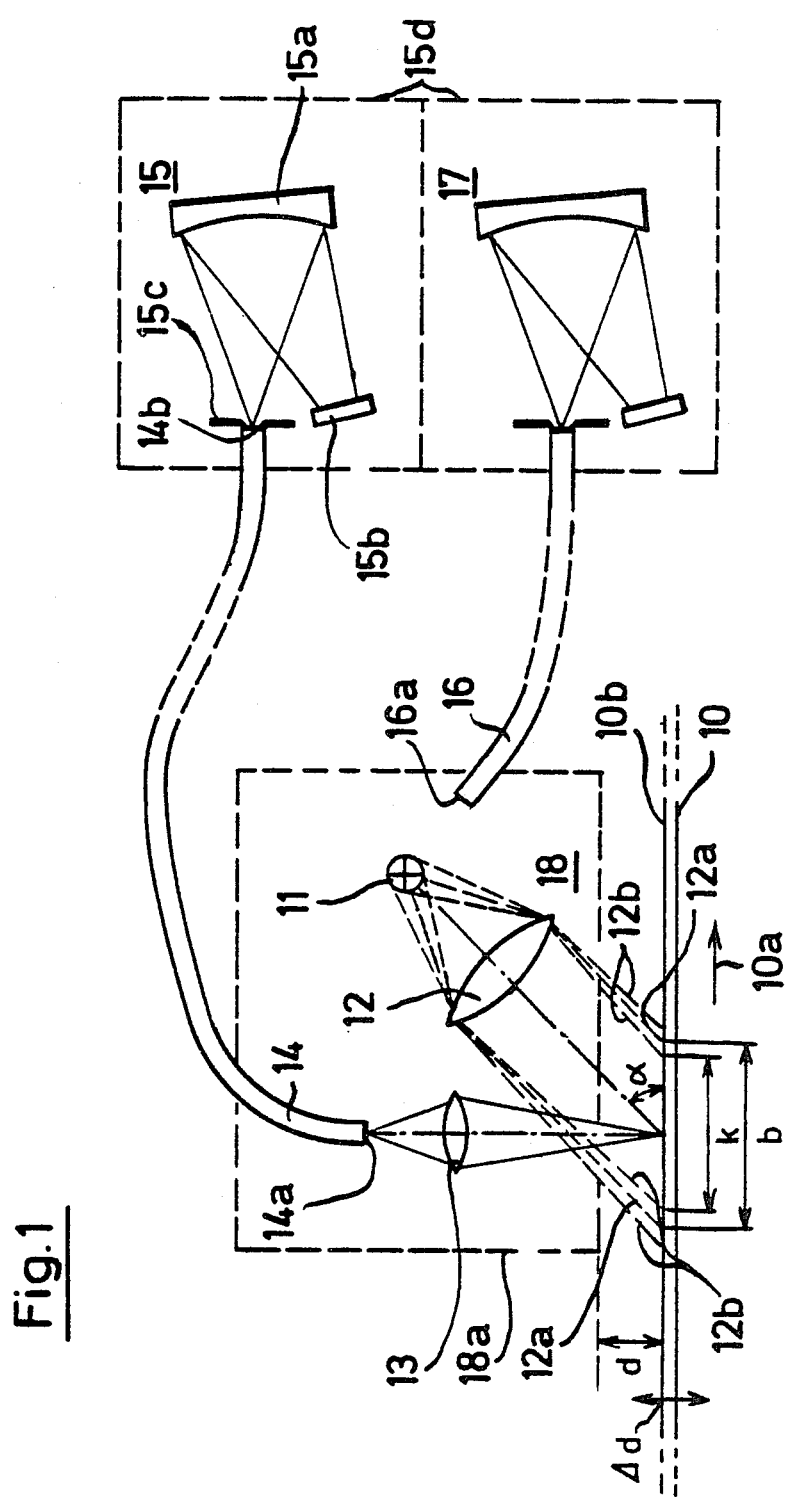
FIG. 1 is a schematic illustrating the principle of the entire measuring apparatus according to the invention; and, FIG. 2 shows an example of the optical configuration of the illuminating and measuring device.

FIG. 1 shows a moving band 10 such as that associated with a paper or printing machine. The band 10 is moved in the direction of the arrow 10a. Its surface 10b moves up and down by a few millimeters in the range $\Delta d$; that is, the band flutters at the locations where there is room to accommodate a measuring device or measuring head 18 for determining the reflectance capacity or the color values. In known measuring apparatus, this fluttering, that is, the distance varying by $\Delta d$ between the measuring head 18 and the surface 10b of the test object, affects the reflectance or color values to the extent of a multiple of what the human eye is capable of perceiving as a difference.

According to the invention, the region of the band surface 10b at which the measurement is to be made is illuminated by a light source 11, which is disposed in the focus of the condenser 12. If the light source 11 were a point, then the resultant beam after the condenser 12 would be an exactly parallel beam of light having boundary lines 12a assuming that imaging errors of the condenser are not considered. The portion of the test object surface 10b illuminated in this manner is called the irradiated area b. Because of the spread of the light source, however, there is a divergence, which causes a distance-dependent edge deterioration between the lines 12b. Nevertheless, within a core region k the ideal conditions are still satisfied, so that in this region the intensity of illumination of the test object surface does not depend on the distance d of the test object surface 10b from the measuring head 18, but instead depends only on the angle $\alpha$ between the optical axis of the illuminating device and the test object surface. This angle, however, remains practically constant, even if the distance d varies.

The light remitted from the band surface 10b is detected in part by the measuring device which comprises the lens 13, the fiber-optic light conductor 14 and the diode-array spectrometer 15. The optical conditions for detecting the reflected radiation will be explained in conjunction with FIG. 2. The diode-array spectrometer 15 is known from published German patent application DE-OS No. 32 15 879, for instance, and comprises the holographic concave grating 15a and the diode array 15b. In the embodiment shown, the entry slit 15c is illuminated by the end 14b of the fiber-optic light conductor 14. If the light conductor comprises a plurality of optical fibers, these are arranged among one another in front of the slit. However, the light conductor, which is not shown to scale in the drawing, may also comprise only a single fiber.

In particular if a pulsed light source is used for the light source 11, it is necessary for the spectrum of each pulse to be received for comparison purposes. This is done by the fiber-optic light guide 16, the inlet surface 16a of which is exposed directly to the radiation, for instance in the vicinity of the light source. The fiber-optic light guide 16 leads to a second diode-array spectrometer 17. The spectra received by the spectrometers are evaluated and the reflectance and color values are calculated in a known manner.

Figure 2:
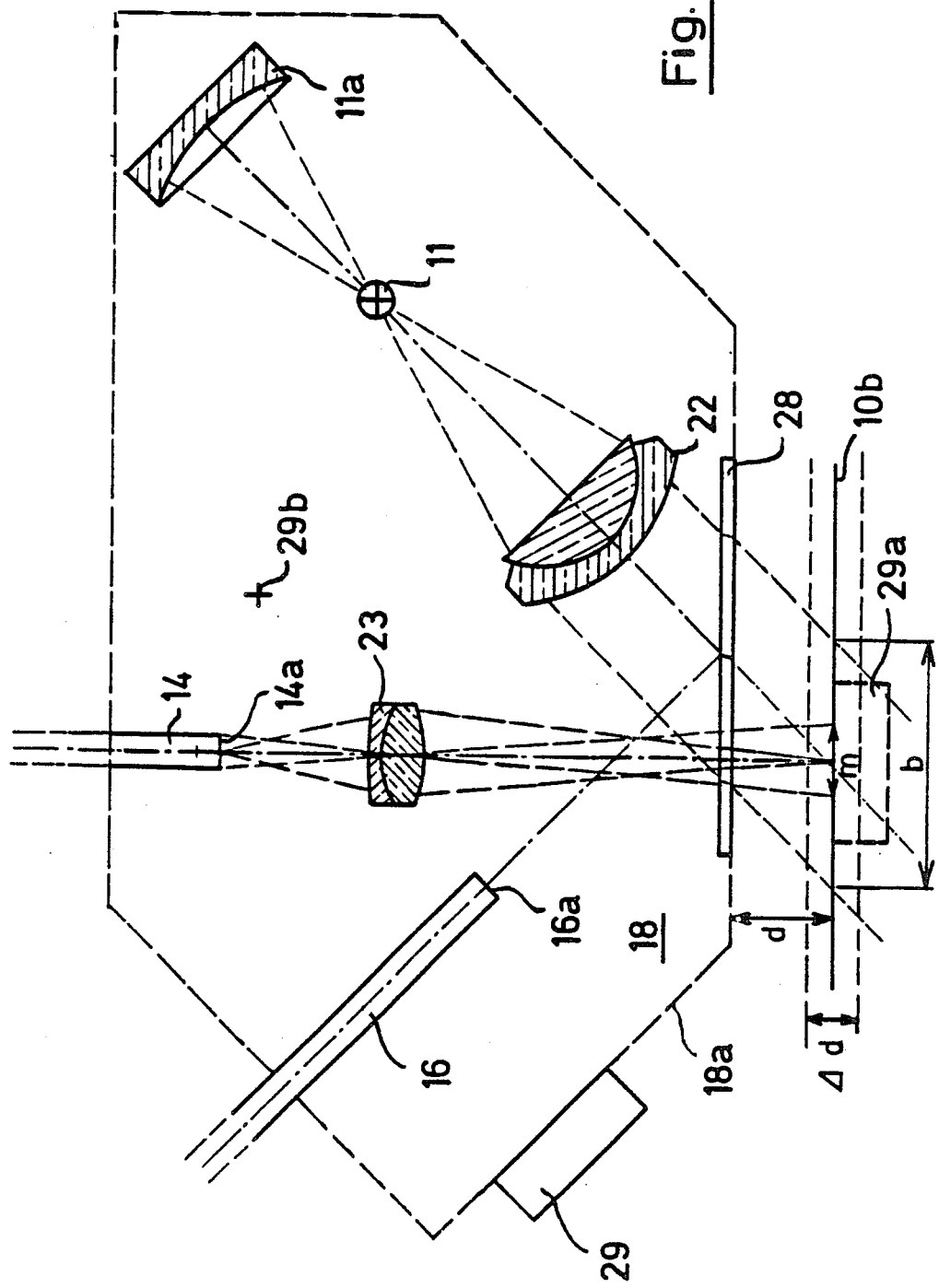

FIG. 2 shows an embodiment of the optical structure of the illuminating and measuring apparatus in more detail. The light source is again identified by reference numeral 11. A double-lens objective is used as the condenser 22, in particular for the purpose of obtaining low chromatic image errors. The band surface is again shown at 10b, and the illuminated irradiated area thereon is again identified with b. For energy reasons, a short-arc discharge lamp is preferably used as the light source, an example being Osram model XBO 75. In the case of bands or similar surfaces that are fast-moving, it is particularly suitable to use a flash lamp, such as Heimann model BGS 29027, because it enables short measurement times. Discharge lamps of this type typically exhibit an irregular variation of the arc position, which also changes the illuminating beam. This effect is lessened by providing the concave mirror 11a, which forms an image of the arc. If the arc drifts, then its mirror image drifts in the opposite direction, so that overall the symmetry is maintained virtually unchanged.

A window 28 which closes off the measuring head 18 is located between the condenser 22 and the test object surface 10b. A portion of the illuminating beam is necessarily reflected at this window; this reflected portion is utilized for the compensation spectrum, and the inlet surface 16a of the fiber-optic light guide 16 is arranged so as to receive a portion from the middle of the core region k. This kind of arrangement is particularly advantageous if maximal accuracy of measurement is important.

A double-lens objective 23 is also used in the measuring instrument for the sake of attaining as good a correction as possible, particularly of chromatic image errors. The objective 23 need not form a sharp image of the band surface 10b on the inlet surface 14a of the light conductor 14; instead, its essential task is, in cooperation with the inlet surface 14a, to limit the size of the measuring area m on the test object surface. This measuring area m can be varied by varying the distance of the objective 23 from the band surface. However, the measuring area m must always be located inside the core region k (see FIG. 1) of the irradiated area b. The inlet surface 14a may be replaced by some other limiting surface; the only important factor is that the aperture be constant; that is, the spatial angle encompassed by the measuring apparatus must be constant, and thus independent of the distance d between the band surface 10b and the illuminating and measuring apparatus 18.

In the embodiment shown, a 45/0 geometry is used, which is typical in reflectance and color measuring technology. Other kinds of geometry are also possible. In FIG. 2, which is enlarged approximately on a scale of 1.5 : 1, the irradiated area b has dimensions of approximately 20 mm perpendicular to the plane of the drawing and approximately 30 mm in the plane of the drawing. The measuring area may be adjusted to a diameter of between 3 and 10 mm. In the event of distance variations $\Delta d$ of the band surface of up to $\pm 4.5$ mm, the color tolerances for a white surface are within $\Delta E^*_{ab} \leq 0.3$ (according to DIN 6174).

It is also possible to combine one illuminating device with a plurality of measuring instruments for various angles, each measuring instrument being connected to a spectrometer. This is especially advantageous if the objects to be tested have glossy characteristics.

All the parts of the illuminating and measuring instrument 18 can be combined in one housing 18a which is connected to the spectrometers 15 and 17 via the fiber-optic light conductors 14 and 16, respectively. The spectrometers can then be accommodated in a second housing 15d, together with the supply of current for the light source 11, so that they can be set up at some distance from the location where measurements are made. It is also advantageous for the housing 18a to be mounted in a pivoting device (not shown) above the band 10, so that it can be pivoted out of its position above the band to facilitate placement of a color or white standard 29a for calibration at a mean distance d in front of the window 28. This standard is pivotable about the axis 29b, and when it is not in use is located in the position 29, where its surface is protected from dust and the like.

The reflectance measuring apparatus described above is not only suitable for making measurements on moving surfaces; it can also be advantageously used for all other reflectance measurements whenever it is not possible to place the test objects to be measured against a measurement aperture as is otherwise usually the case. The reflectance measuring apparatus is particularly suitable for all contactless measurements, for example, on liquid dyes.

It is understood that the foregoing description is that of the preferred embodiments of the invention and that various changes and modifications may be made thereto without departing from the spirit and scope of the invention as defined in the appended claims.

What is claimed is:

1. A reflectance measuring apparatus for making contactless measurements on a moving surface of a sample moving in a given direction, the surface fluttering transversely to said direction within a predetermined range, the apparatus being mounted a predetermined distance from said sample and comprising:

a single stationary light source for supplying light;

light directing means for directing said light onto said surface so as to define an irradiated area and a measurement area within said irradiated area wherein the intensity of illumination is virtually independent of said distance for flutter excursions within said range;

a measuring device for receiving radiation returned from said measurement area; and said light directing means including a condenser defining a focus and said light source being mounted at said focus; and, said condenser directing said light onto said surface in a substantially parallel beam to also define a core area wherein said intensity is virtually independent of said distance and to define said measurement area to be less than said core area when said surface is at its farthest distance of said range from said measuring device.

2. The reflectance measuring apparatus of claim 1, said light directing means further comprising a concave mirror having a focus lying in said light source and being mounted on the side of said light source facing away from said condenser.

3. The reflectance measuring apparatus of claim 1, said measuring device comprising:
a receiver for receiving the radiation returned from said measurement area; and,
transmitting means for transmitting the returned radiation entering said measuring device to said receiver, said transmitting means including limiting surface means for admitting said returned radiation; and, a lens disposed between said limiting surface and said measurement area.

4. The reflectance measuring apparatus of claim 1, comprising:
a diode-array spectrometer for receiving the radiation returned from said measurement area;
said measuring device including a lens for transmitting said returned radiation;
said apparatus further comprising a light conductor for transmitting said returned radiation from said lens to said spectrometer; and,
said light conductor having an inlet end defining a limiting surface for admitting the returned radiation.

5. The reflectance measuring apparatus of claim 3, comprising a housing for accommodating said light source, said condenser, said concave mirror and said limiting surface means, said housing having a window for admitting said returned radiation.

6. The reflectance measuring apparatus of claim 5, said condenser being mounted in said housing so as to cause said light from said light source to pass through said window and from which a portion of said light is reflected; said apparatus comprising a reference measuring device for receiving a section of the core region of said reflected light.

7. The reflectance measuring apparatus of claim 3, comprising:
a diode-array spectrometer for receiving the radiation returned from said measurement area;
said measuring device including a lens for transmitting said returned radiation;
said apparatus further comprising a light conductor for transmitting said returned radiation from said lens to said spectrometer;
said light conductor having an inlet end defining a limiting surface for admitting the returning radiation;
a housing for accommodating said light source, said condenser, said concave mirror and said limiting surface means, said housing having a window for admitting said returned radiation;
said condenser being mounted in said housing so as to cause said light from said light source to pass through said window and from which a portion of said light is reflected;
said apparatus including a reference measuring device for receiving a section of the core region of said reflected light; and,
a second diode-array spectrometer for said reference measuring device.

8. The reflectance measuring apparatus of claim 1, said apparatus being pivotally mounted for pivoting the same away from said sample, the combination of a standard pivotally mounted so as to be pivoted to a position above said surface corresponding to the mean value of said predetermined distance.

9. The reflectance measuring apparatus of claim 1, said light source being a pulse light source.

10. A reflectance measuring apparatus for making contactless measurements on a surface of a sample, the level of the surface of the sample varying within a predetermined range, the apparatus being mounted a predetermined distance from said surface and comprising:
a single stationary light source for supplying light;
light directing means for directing said light onto said surface so as to define an irradiated area and a measurement area within said irradiated area wherein the intensity of illumination is virtually independent of said distance for flutter excursions within said range;
a measuring device for receiving radiation returned from said measurement area; and,
said light directing means including a condenser defining a focus and said light source being mounted at said focus; and, said condenser directing said light onto said surface in a substantially parallel beam to also define a core area wherein said intensity is virtually independent of said distance and to define said measurement area to be less than said core area when said surface is at its farthest distance of said range from said measuring device.

* * * * *